United States Patent [19]
Carrillo

[11] Patent Number: 5,906,626
[45] Date of Patent: May 25, 1999

[54] SUTURE DEPRESSOR

[76] Inventor: Hipolito Carrillo, P.O. Box 404, Guaynabo, Puerto Rico 00970

[21] Appl. No.: 08/908,745

[22] Filed: Aug. 7, 1997

[51] Int. Cl.$^6$ .................................................. A61B 17/04
[52] U.S. Cl. .............................................................. 606/148
[58] Field of Search ................................ 606/148, 146, 606/139, 205–209; 223/103; 112/80.03, 169; D24/145

[56] References Cited

U.S. PATENT DOCUMENTS

| | | | |
|---|---|---|---|
| D. 353,002 | 11/1994 | Tovey | 606/148 X |
| 2,595,086 | 4/1952 | Larzelere | 606/148 |
| 2,665,692 | 1/1954 | L'Esperance | 606/148 |
| 4,819,640 | 4/1989 | Narayanan et al. | 606/148 |
| 5,792,177 | 8/1998 | Kaseda | 606/148 X |

*Primary Examiner*—Michael Buiz
*Assistant Examiner*—VIkki Trinh
*Attorney, Agent, or Firm*—Douglas E. Mackenzie

[57] ABSTRACT

A new suture depressor for suturing tissues without the risk of harm to the tissues commonly encountered with the use of forceps. The inventive device includes a handle having distal and proximal ends. A flattened portion is formed at the distal end at an acute angle relative to a longitudinal axis of the handle and includes a pair of spaced-apart projections which extend parallel one to the other from opposite ends of a flattened portion edge.

7 Claims, 1 Drawing Sheet

SUTURE DEPRESSOR

BACKGROUND OF THE INVENTION

1. Field of the Invention

The present invention relates to suturing instruments and more particularly pertains to a new suture depressor for suturing tissues without the risk of harm to the tissues commonly encountered with the use of forceps.

2. Description of the Prior Art

The use of suturing instruments is known in the prior art. More specifically, suturing instruments heretofore devised and utilized are known to consist basically of familiar, expected and obvious structural configurations, notwithstanding the myriad of designs encompassed by the crowded prior art which have been developed for the fulfillment of countless objectives and requirements.

Known prior art suturing instruments include U.S. Pat. No. 5,176,691; U.S. Pat. No. 5,087,263; U.S. Pat. Des. No. 353,002; U.S. Pat. No. 4,961,741; U.S. Pat. No. 4,641,652 and U.S. Pat. No. 4,602,635.

While these devices fulfill their respective, particular objectives and requirements, the aforementioned patents do not disclose a new suture depressor. The inventive device includes a handle having distal and proximal ends, a flattened portion formed at the distal end and a pair of spaced-apart projections integrally formed at a flattened portion edge.

In these respects, the suture depressor according to the present invention substantially departs from the conventional concepts and designs of the prior art, and in so doing provides an apparatus primarily developed for the purpose of suturing tissues without the risk of harm to the tissues commonly encountered with the use of forceps.

SUMMARY OF THE INVENTION

In view of the foregoing disadvantages inherent in the known types of suturing instruments now present in the prior art, the present invention provides a new suture depressor construction wherein the same can be utilized for suturing tissues without the risk of harm to the tissues commonly encountered with the use of forceps.

The general purpose of the present invention, which will be described subsequently in greater detail, is to provide a new suture depressor apparatus and method which has many of the advantages of the suturing instruments mentioned heretofore and many novel features that result in a new suture depressor which is not anticipated, rendered obvious, suggested or even implied by any of the prior art suturing instruments either alone or in any combination thereof.

To attain this, the present invention generally comprises a handle having distal and proximal ends, a flattened portion formed at the distal end and a pair of spaced-apart projections integrally formed at a flattened portion edge.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new suture depressor apparatus and method which has many of the advantages of the suturing instruments mentioned heretofore and many novel features that result in a new suture depressor which is not anticipated, rendered obvious, suggested, or even implied by any of the prior art suturing instruments, either alone or in any combination thereof.

It is another object of the present invention to provide a new suture depressor which may be easily and efficiently manufactured and marketed.

It is a further object of the present invention to provide a new suture depressor which is of a durable and reliable construction.

An even further object of the present invention is to provide a new suture depressor which is susceptible of a low cost of manufacture with regard to both materials and labor, and which accordingly is then susceptible of low prices of sale to the consuming public, thereby making such suture depressor economically available to the buying public.

Still yet another object of the present invention is to provide a new suture depressor which provides in the apparatuses and methods of the prior art some of the advantages thereof, while simultaneously overcoming some of the disadvantages normally associated therewith.

Still another object of the present invention is to provide a new suture depressor for suturing tissues without the risk of harm to the tissues commonly encountered with the use of forceps.

Yet another object of the present invention is to provide a new suture depressor which includes a handle having distal and proximal ends, a flattened portion formed at the distal end and a pair of spaced-apart projections integrally formed at a flattened portion edge.

Still yet another object of the present invention is to provide a new suture depressor that provides a unique quirurgical instrument that avoids tissue damage by pushing the tissue to be sutured instead of pulling it, thereby creating fixation of the body area undergoing suture.

Even still another object of the present invention is to provide a new suture depressor that is advantageously used to suture weak body tissues such as skin, spleen, bladder and the like.

Even still another object of the present invention is to provide a new suture depressor that is advantageously used to suture hard to reach areas.

Still yet another object of the present invention is to provide a new suture depressor that provides for a greater visual field while suturing.

Even still another object of the present invention is to provide a new suture depressor that is advantageously used in dental as well as general surgery.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figures 1, 2:
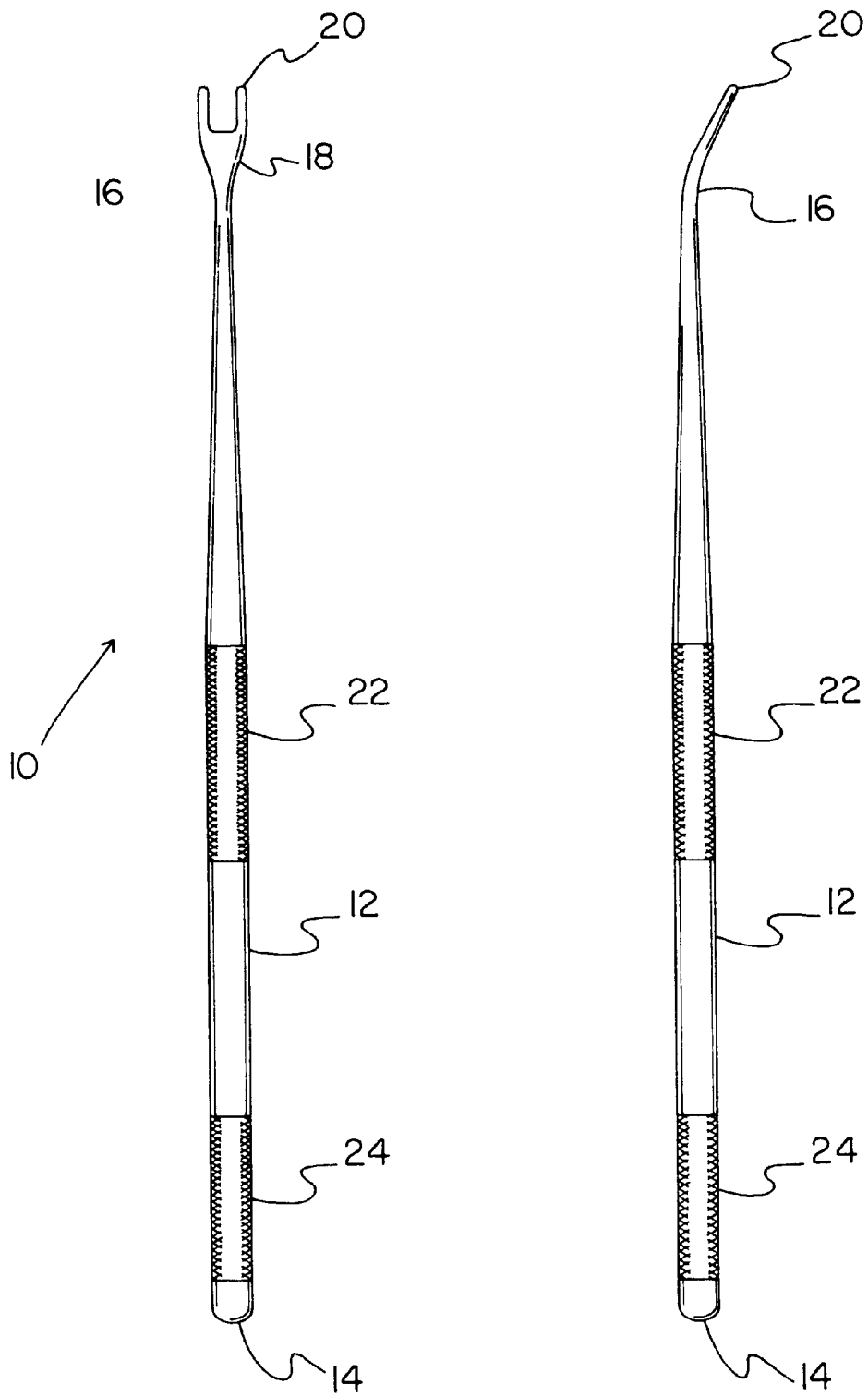
FIG. 1 is a top isometric view of a new suture depressor according to the present invention.
FIG. 2 is a side isometric view thereof.

With reference now to the drawings, and in particular to FIGS. 1 and 2 thereof, a new suture depressor embodying the principles and concepts of the present invention and generally designated by the reference numeral 10 will be described.

With reference to FIG. 1, it will be noted that the suture depressor 10 comprises a handle 12 of cylindrical construction having a distal end 16 and a proximal end 14 and a means for depressing the suture disposed at the distal end 16 of the handle 12. A flattened portion 18 includes a first end 26 integrally formed at the handle distal end 16 and a second end 27. The flattened portion second end 27 includes an edge 28 extending perpendicularly from a longitudinal axis formed by the handle 12. The suture depressor 10 is preferably manufactured of stainless steel for reuse and of plastic for disposable use and measures from 6 to 10 inches in length, dependent upon the application.

With continued reference to FIG. 1 there is shown the means for depressing the suture including a pair of spaced-apart projections 20 extending from opposing ends of the a flattened portion edge 28. The projections 20 are shown extending parallel one to the other and spaced $5/16^{th}$ of an inch apart. The projections 20 are shown spaced $5/16^{th}$ of an inch apart. A first gripping means for gripping the handle is shown including a first knurled section 24. A second gripping means for gripping the handle is shown disposed intermediate the first knurled section 24 and the proximal end 14 including a second knurled section 22.

With reference to FIG. 2 there is shown the means for depressing the suture including the flattened section 18 and the projections 20. The flattened portion 18 and the projections 20 are shown acutely angled from the longitudinal axis of the handle 12.

In use, the suture is depressed by the projections 20 and flattened portion 18 to join the tissues to be sutured.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A suture depressor for use in depressing a suture comprising:

a handle having distal and proximal ends;

a flattened portion having a first end integrally formed at the distal end and a second end having an edge disposed perpendicularly from a longitudinal axis of the handle;

pair of spaced-apart projections extending from opposing ends of the second end edge, the projections being disposed parallel one to the other; and wherein the flattened portion and the projections form a U-shape.

2. The suture depressor of claim 1, wherein the projections are spaced $5/16^{th}$ of an inch apart.

3. The suture depressor of claim 1, wherein the flattened portion is disposed at an acute angle relative to the longitudinal axis of the handle.

4. The suture depressor of claim 1, wherein the handle further comprises a first gripping means for gripping the handle.

5. The suture depressor of claim 4, wherein the first gripping means further comprises a first knurled section.

6. The suture depressor of claim 4, wherein the handle further comprises a second gripping means for gripping the handle disposed intermediate the first gripping means and the proximal end.

7. The suture depressor of claim 6, wherein the second gripping means further comprises a second knurled section.

* * * * *